United States Patent [19]

Schlawne

[11] Patent Number: 5,113,697
[45] Date of Patent: May 19, 1992

[54] PROCESS AND APPARATUS FOR DETECTING DISCONTINUITIES ON LONG WORKPIECES

[75] Inventor: Friedheim Schlawne, Kerben, Fed. Rep. of Germany

[73] Assignee: Mannesmann AG, Düsseldorf, Fed. Rep. of Germany

[21] Appl. No.: 463,609

[22] Filed: Jan. 12, 1990

[30] Foreign Application Priority Data

Jan. 13, 1989 [DE] Fed. Rep. of Germany ....... 3901238
Dec. 22, 1989 [DE] Fed. Rep. of Germany ....... 3943226

[51] Int. Cl.⁵ .............................................. G01N 29/04
[52] U.S. Cl. ...................................... 73/602; 73/622; 73/637; 73/638
[58] Field of Search ................. 73/602, 622, 637, 638, 73/640, 598, 618, 643, 599

[56] References Cited

U.S. PATENT DOCUMENTS

| | | | |
|---|---|---|---|
| 3,166,930 | 1/1965 | Zollmer | 73/622 |
| 3,961,523 | 6/1976 | Cornforth | 73/622 |
| 4,065,960 | 1/1978 | Grabendorfer et al. | 73/622 |
| 4,289,033 | 9/1981 | Prause et al. | 73/637 |
| 4,497,210 | 2/1985 | Uchida et al. | 73/602 |
| 4,641,531 | 2/1987 | Reeves et al. | 73/622 |
| 4,817,431 | 4/1989 | Schlawne | 73/600 |

FOREIGN PATENT DOCUMENTS

| | | |
|---|---|---|
| 2605405 | 8/1977 | Fed. Rep. of Germany . |
| 3218453 | 11/1983 | Fed. Rep. of Germany . |
| 192859 | 11/1982 | Japan ..................... 73/602 |
| 58-186046 | 10/1983 | Japan . |
| 2027199 | 2/1980 | United Kingdom ................... 73/622 |

OTHER PUBLICATIONS

*Ultrasonic Inspection of Tubes;* Ultrasonics Jul.-Sep. 1964 pp. 109-119 R. F. Hanstock.
*Difettoscopia a ultrasuoni di tubi a forte spessore di parete mediante sonde interne* dell' Istituto Sperimentale dei Metalli Leggeri Nov. 1967 M. Robba pp. 567-572.

Primary Examiner—Hezron E. Williams
Assistant Examiner—Craig Miller
Attorney, Agent, or Firm—Nils H. Ljungman & Associates

[57] ABSTRACT

Process and apparatus for the detection of discontinuities in long workpieces such as pipes, tubes, rods and bars using vibrational transducer equipment transmitter pulses in separate directions about the workpiece.

19 Claims, 7 Drawing Sheets

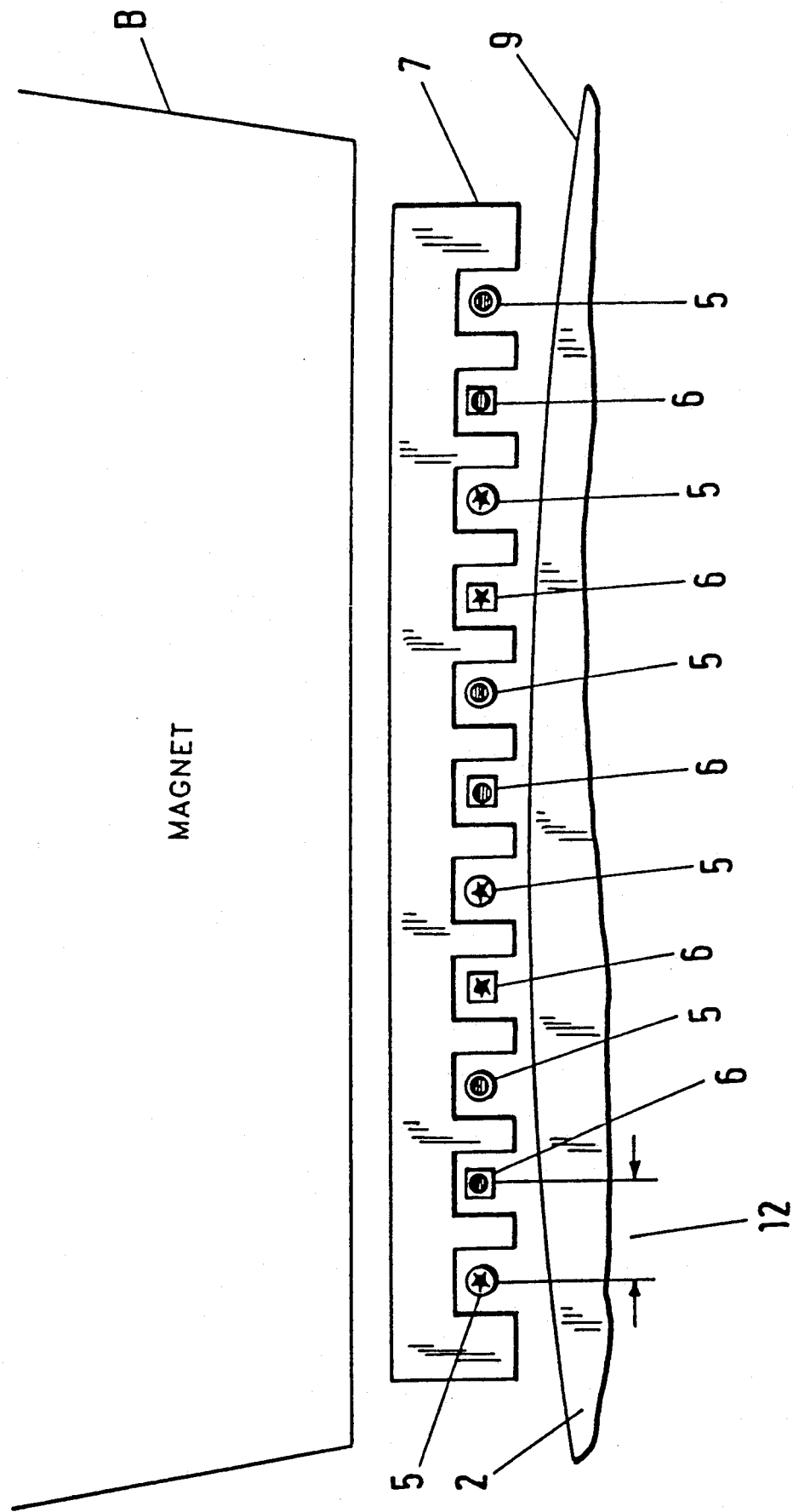

5,113,697

PROCESS AND APPARATUS FOR DETECTING DISCONTINUITIES ON LONG WORKPIECES

BACKGROUND OF THE INVENTION

1. Field of the Invention

This invention relates to a process for the detection of discontinuities on long workpieces, in particular on tubes, rods and bars, as well as to an apparatus for the execution of the process.

2. Background Information

German Laid Open Patent Application No. 26 05 405 discloses a process for the ultrasonic inspection of tubes to detect defects having various orientations, in which Lamb or plate waves are generated and travel several times around the circumference of the tube, and the attenuation of the circulating waves is evaluated. In this process, neither a rotation of the tube nor of the transducer around the tube is necessary, as is required with many current conventional processes. With this configuration, defects having almost any orientation can be detected. Since this is an integral process, however, the defect detection sensitivity is essentially determined by the surface quality of the test piece. For longitudinally-oriented defects, there are reflections from the defects. The reflected wave pulses may interfere with the circulating waves, and there is no assurance that these defects will necessarily be detected. Moreover, the interference-free detection of the signal reflected at a defect is desirable, since a pulse reflection process is usually more sensitive than an integral or direct transmission process.

Such a pulse reflection process using electrodynamically generated surface waves, which can be combined with a transmission process, is disclosed in DE-OS 32 18 453, and is used to examine the running surfaces of railroad rails. In that case, transducers are used which act both bidirectionally and unidirectionally. With bilaterally active transducers, a secure separation of the reflection indications from the indications of the primary circulating waves is not always possible, which is particularly true for long workpieces having a small diameter. Moreover, for example, in the examination of thin-walled tubes using plate waves, there is a danger of exciting external modes such as sound or noise modes, which also circulate several times around the test piece, which have a group speed different from the test mode, and whose indications cannot be distinguished from reflection indications. The use of unidirectional transducers, may make it possible to suppress the indications of primary circulating waves and only to evaluate reflected pulses; however, these transducers may require that test shots or pulse or other excitation in both circumferential directions be conducted one after another, and thus result in a lower test speed or in other words a greater time requirement to make a test. Moreover, the expense for electronic equipment, calibration and adjustment of such a test apparatus which works with unidirectional transducers is usually correspondingly high.

A transducer used for inspection with circulating waves which takes advantage of the destructive interference at the site of the receiver is disclosed in Patent Abstracts of Japan, P 253, Feb. 9, 1984, Vol. 8, No. 31. However, such an arrangement may only be used with difficulty for the inspection of the external surface of tubes, rods and bars, since it is often almost impossible to keep the destructive interference in a 180 degree orientation under the operating conditions of a manufacturing plant.

German Laid Open Patent Application No. 36 22 500 discloses a process in which, for the specified measurement of amplitudes of wave pulses circulating tangentially, the receiver signals are synchronized with burst signals of the same frequency, suitable duration and starting delay. A prerequisite for the proposed process, however, is that the precise position of the indication of the primary circulating waves is known, by means of the knowledge of the geometric orientation of transmitter and receiver, and the sound velocity of the circulating wave pulses. For this reason, the process of the prior art is not suitable for the recognition of reflection indications, since the defects or the discontinuities in the workpiece can be located at any point on the circumference of the test piece.

OBJECT OF THE INVENTION

The object of the invention is a process for the detection of discontinuities on long workpieces, in particular on tubes, rods and bars, which minimizes or eliminates the above-mentioned problems and by means of which discontinuities, in particular longitudinally oriented discontinuities, can be detected with great or improved accuracy and at a high inspection speed.

SUMMARY OF THE INVENTION

This object is achieved by the embodiments of the invention, by means of a process of the type described above having the features indicated infra.

The above-mentioned problems are substantially eliminated by the process according to the invention. If a transducer simultaneously emits a wave pulse in both circumferential directions of the test piece, these wave trains encounter one another often at two points on the circumference: substantially at the transmitting transducer itself and in the position located usually precisely 180 degrees opposite on the circumference. If the receiving transducer is positioned precisely where the two wave trains produce destructive interference, then the receiver will measure nothing on a defective test piece.

Now, however, in the presence of a longitudinally-oriented discontinuity on the circumference of the test piece, there is typically always a reflection of a portion of the circulating waves, which reflection leads to a sequence of receiver signals. Likewise, receiver signals occur if a discontinuity leads to a different attenuation of the two wave pulses travelling in the two circumferential directions, i.e. if the discontinuity produces a different reflection of the pulse running in the opposite direction.

With the process described here, it is particularly advantageous that each discontinuity is scanned several times, and that on each revolution there is a repeated reflection at a longitudinally-oriented discontinuity, whereby reflected signals interfere with waves already reflected during the preceding revolution, so that the signal sequence for a test shot can be escalated as a function of the damping of the revolving waves and the diameter of the test piece.

On account of the multiple revolutions and the multiple reflection, in the presence of a defect, many signals are measured during each test cycle. To evaluate more than one indication and to achieve a good signal-to-noise ratio, the invention discloses the generation of a burst signal, the period of which is preferably less than one-quarter of the revolution time of the uninterfered circulating waves. Alternatively thereby for each clock pulse, the sender which operates the transmitting transducer and the signal source which produces the burst signal, is activated by the same clock pulse. Yet alternatively thereby for each clock pulse, the sender which operates the transmitting transducer and the signal source which produces the burst signal are operated by the same clock pulse. The use of a burst signal with a very high pulse duty factor is particularly advantageous. If the analog signal and this burst signal are conducted to a peak detector, the latter determines, in each time window, a maximum value which is retained at the output of the peak detector until a new maximum value is determined in the next time window. On account of the selection according to the invention of the period of the burst signal, it is guaranteed both that the reflection signals can be detected and that there can also be a measurement of the zero line, since individual time windows are located between the reflection signals.

The measurement of the zero line is very desirable with the use of electrodynamic transducers, since only in that way can any noise be detected, and an evaluation be made of the readings exceeding the zero line. As a result of the selection according to the invention of the length of the burst signal, many reflection readings are determined, so that a suitable integration can be made. The method has the advantage over a complete digitization of the analog receiver signal with a high sampling rate that the information can be reduced to the amount required by the hardware, and thus, depending on the order of magnitude, only 50 to 100 values preferably need to be read into the computer and processed there. Therefore this method makes possible a very rapid evaluation of the receiver signals, so that the cycle frequency is essentially determined by the decay of the revolving wave and not by the time it takes for evaluation.

For discontinuities located exactly underneath the transmitting transducer, or exactly on the opposite site, under certain conditions there can be extinctions of the reflection signals running in both directions at the site of the receiver. To remedy this, a refinement of the invention proposes that wave pulses running in both circumferential directions be generated alternately in the test cycle at two sites separated from one another in the circumferential direction, whereby the site of the reception for the reflected pulse is different from that of the damped pulse, and the corresponding sequence of receiver signals is evaluated separately. With this refined process, by an evaluation of the damping of the waves, it is possible in particular to detect discontinuities having a different orientation in relation to the axis of the test piece. This refinement of the process can simultaneously serve as a test of the coupling interface for probe-to-specimen contact. The sensitive longitudinal defect detection capability according to the process embodied by the invention remains fully realized.

Electrodynamic transducers which preferably have separate transmitting and receiving coils are typically used to execute the process. These transducers according to the invention are characterized by the fact that the transmitting and receiving windings of the coil system are interleaved or interwound with one another on the same bobbin, so that the transmitting and receiving windings are offset from one another by one-quarter of the wavelength of the waves transmitted. Thus the wave trains running in both circumferential directions preferably have a phase relationship which is opposite at the site of the receiving transducer, and thus produce destructive interference.

For the combined process, in one circumferential plane, there are two fixed transducers offset from one another over the circumference of the test piece, and the sequence of the receiving signals of both transducers is typically inputted into an evaluation unit.

In summary, one aspect of the invention resides broadly in a process for the detection of vibrationally determinable discontinuities in elongated workpieces such as pipes, tubes, rods and bars, said process comprising the steps of: positioning the workpiece in relationship to a vibrational transducer transmitting means; generating at least two vibrational signals with the vibrational transducer transmitting means and directing the generated vibrational signals at least around a peripheral portion of the elongated workpiece on which detection of discontinuities i being conducted; projecting the vibrational signals generated by the vibrational transducer means at least as two transmitted signals in substantially different directions about the workpiece; disposing at east one receiving transducer mean at its corresponding at least one predetermined position around the workpiece; said at least one predetermined position being located to receive signals where at least two of the signals transmitted by said transducer means in a workpiece substantially free of any substantial discontinuities would produce at least partial destructive interference between the at least two transmitted signals; said transmitted signals comprising pulses; said transmitted signals having a cycle period of time between pulses which is substantially longer than the time corresponding to the pulse widths; choosing the time from the beginning of one pulse to the beginning of the next pulse of a cycle period of time of said transmitted signals as being a time less than one quarter of the time for a pulse to traverse around a peripheral portion of the elongated workpiece for a workpiece being substantially free of any substantial discontinuities; choosing the length of time of the pulse width of the transmitted signal to be in correspondence with the decay time of a pulse propagating in a workpiece which workpiece is substantially free of any substantial discontinuities; receiving said transmitted at least two generated vibrational signals at said at least one receiving transducer means which receiving transducer means is disposed at said at least one predetermined position; processing at least the received signals to indicate deviations from signals received from a substantially equivalent workpiece being substantially free of any substantial discontinuities in a processing unit; and determining at least the presence of any substantial discontinuities in the workpiece being tested in said processing unit.

Another aspect of the invention resides broadly in an apparatus for a process for the detection of vibrationally determinable discontinuities in elongated workpieces such as pipes, tubes, rods and bars, said apparatus comprising: vibrational transducer transmitting means for generating at least two vibrational signals and directing the generated vibrational signals at least around a peripheral portion of the elongated workpiece on which detection of discontinuities is to be conducted; said vibrational transducer transmitting means comprising means for projecting the vibrational signals generated by the vibrational transducer means at least as two transmitted signals in substantially different directions about the workpiece; at least one receiving transducer mean at its corresponding at least one predetermined position around the workpiece; said vibrational transducer transmitting means for being located at at least one predetermined position for receiving signals; said vibrational transducer transmitting means for being located where at least two of the signals transmitted by said transducer means in a workpiece substantially free of any substantial discontinuities would produce at least partial destructive interference between the at least two transmitted signals; said vibrational transducer transmitting means comprising means for generating said transmitted signals as pulses; said transmitted signals for having a cycle period of time between pulses which is substantially longer than the time corresponding to the pulse widths; said vibrational transducer transmitting means having means for setting the time from the beginning of one pulse to the beginning of the next pulse of a cycle period of time of said transmitted signals for being a time less than one quarter of the time for a pulse to traverse around a peripheral portion of the elongated workpiece for a workpiece being substantially free of any substantial discontinuities; said vibrational transducer transmitting means having means for setting the length of time of the pulse width of the transmitted signal to be in correspondence with the decay time of a pulse propagating in a workpiece which workpiece is substantially free of any substantial discontinuities; said at least one receiving transducer means for receiving said transmitted at least two generated vibrational signals at said at least one receiving transducer means which at least one receiving transducer means is for being disposed at said at least one predetermined position; and a processing unit for processing at least the received signals and for indicating deviations from signals received from a substantially equivalent workpiece being substantially free of any substantial discontinuities; said processing unit comprising means for determining at least the presence of any substantial discontinuities in the workpiece being tested in said processing unit.

BRIEF DESCRIPTION OF THE DRAWINGS

The process according to the invention is described in greater detail in the accompanying drawings, which depict two embodiments and the corresponding apparatus.

FIG. 2 shows a schematic drawing of the transducer according to the invention.

DESCRIPTION OF THE PREFERRED EMBODIMENTS

Figure 1:
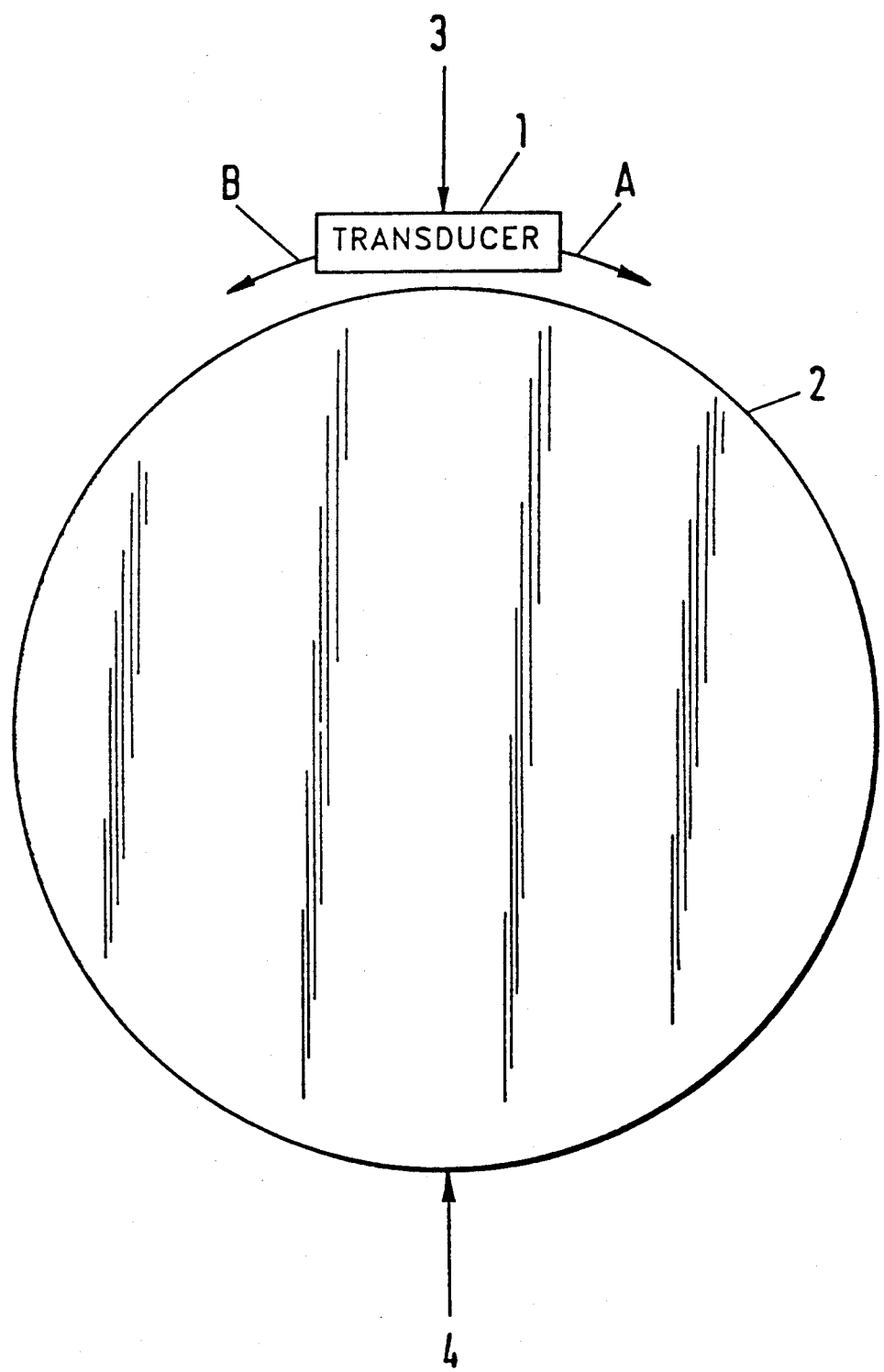
FIG. 1 shows a schematic drawing for the execution of the process according to the invention.

FIG. 1 is a schematic diagram of the apparatus for the execution of the process according to the invention. A transducer 1 located at a specified distance from a test piece 2 simultaneously emits a wave pulse A, B in both circumferential directions of the test piece 2. In this FIG. 1, the wave pulse emitted in the clockwise direction is designated by Index A and the wave pulse emitted in the counterclockwise direction is designated by Index B. Both wave pulses A, B circulate several times in the circumferential direction, and meet at two defined points of the circumference: once at the transducer 1 itself, here designated Position 3, and on the side exactly opposite by 180 degrees, here designated Position 4. The process according to the invention is now characterized by the fact that the receiving transducer is positioned precisely at the point where the two uninterfered wave pulses A, B interfere destructively. For the execution of the process, two configurations are possible, one in which the transducer 1 is only a transmitting transducer, and the receiving transducer (not shown here in FIG. 1) is located in Position 4. This configuration will typically be used only in very rare cases, since the precise positioning and calibration of the receiving transducer may he very difficult. The other possibility is that in the transducer 1, the transmitting and receiving coils 5, 6 (FIG. 2) are interleaved with one another, and are wound so that they are offset from one another by one-quarter of the wavelength of the waves transmitted.

FIG. 2 shows the details of the transducer according to an embodiment of the invention. Between the surface 9 of the test piece 2 and the magnet 8 or the magnet system, there is a bobbin 7. On this bobbin 7, the transmitting and receiving windings 5 and 6 respectively are interleaved or interspersed with one another and wound so that the distance 12 between two neighboring windings is one-quarter of the wavelength.

Figure 3A:
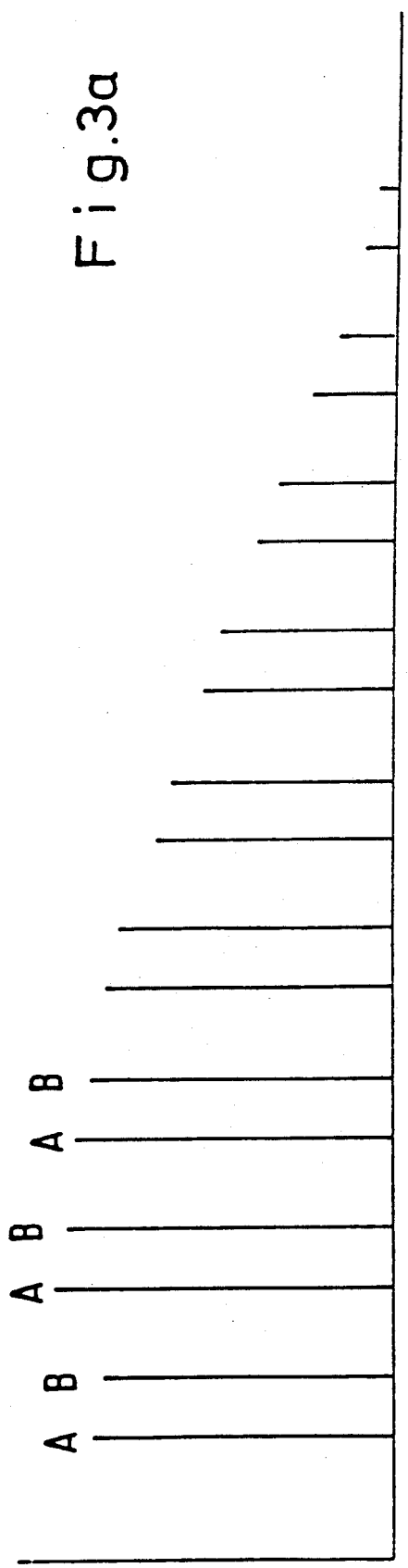
FIG. 3a shows the analog receiver signal with a sequence of reflection readings.

FIG. 3a shows a schematic diagram of the amplitudes of a sequence of reflected signals for a test shot. In the illustrated example the discontinuities at which the two wave trains A, B are reflected, are approximately on the side opposite the transmitter, since the amplitudes differ only very slightly. This schematic diagram very clearly shows the escalation effect, which always occurs when the reflected signal of the two wave trains A, B interferes constructively with the waves reflected during the preceding revolution. Thus, as a function of the time and of the number of revolutions, the damping effect is initially over-compensated, and only after the peak is passed does the damping influence predominate with each additional revolution.

Figure 3B:
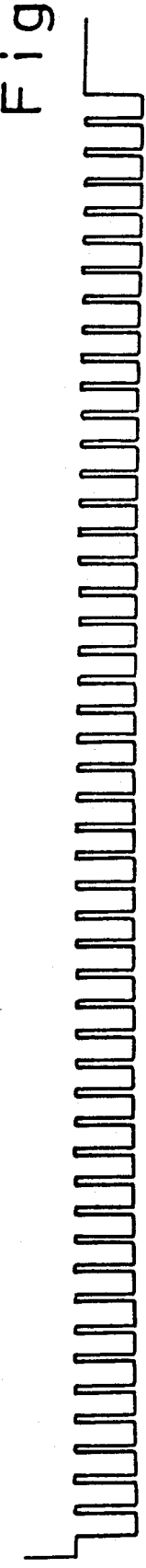
FIG. 3b shows the burst signal according to the invention.
Figure 3C:
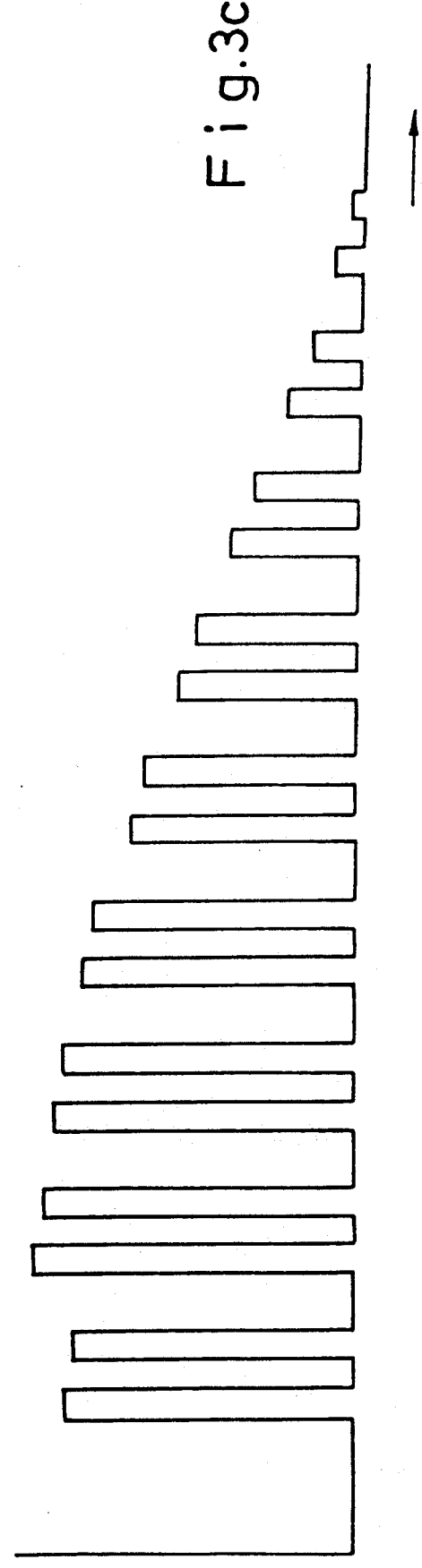
FIG. 3c shows the output signal of the peak detector.

FIG. 3b illustrates the burst signal belonging to the analog signal according to the invention Important in this figure is the very different pulse duty factor of the burst signal, which differs significantly from a typical conventional 1:1 ratio. The term "pulse duty factor" as used here is defined as the ratio of the time interval in which the peak detector is active to the time interval in which the peak detector is not active. According to the invention, this ratio should be as large as possible. The analog signal and the burst signal are conducted to a peak detector, whose output signal is illustrated in FIG. 3c.

The pulses according to an embodiment or embodiments of the invention may be relatively short in comparison to the time between pulses. This relationship of the pulses may be applied to any and all embodiments of the invention.

Figure 4:
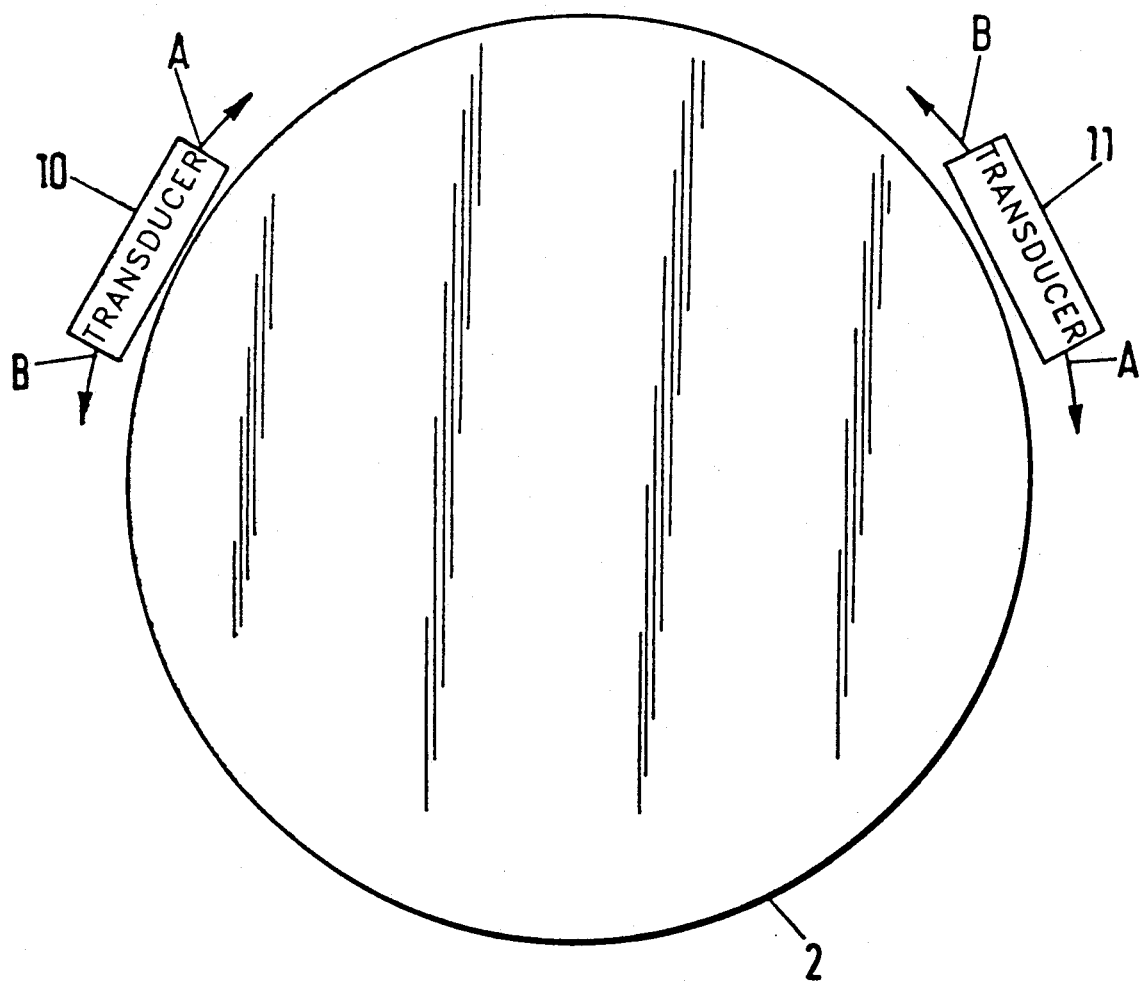
FIG. 4 shows a schematic diagram of the combined process according to the invention.

FIG. 4 shows the combined process according to the invention, in which the pulse reflection process and the transmission process are used simultaneously. For that purpose, there are two separate electrodynamic transducers 10, 11 located on the circumference of the test piece 2. Both transducers 10, 11 have transmitting and receiving windings 5 and 6 respectively offset by one-quarter of the wavelength (See FIG. 2). The transmitter coils of the two transducers 10, 11 are operated in alternation. In the first clock pulse, the transmitting coil of the transducer 10 located on the left transmits, and the receiving coil of the transducer 11 located on the right measures the amplitudes of the circulating waves, and conducts the sequence of receiver signals to an evaluation unit (not shown here). Simultaneously, the receiving coil of the transducer 10 located on the left measures signals, i.e. reflection signals or signals which are caused by the non-uniform attenuation of the waves circulating in both directions, and also conducts these signals to the evaluation unit. The signals measured in the receiving coil of the transducer 11 located on the right, e.g. the sum of the amplitudes of the first two peaks, can also be used for a rough coupling check that is interface check or rather check of probe-to-specimen contact of the receiving coil of the transducer 10 located on the left, since the latter is integrated into the transmitting coil of the transducer 10. For the second clock pulse, there is an exchange of the generation or reception of the two transducers 10, 11.

Figure 5:
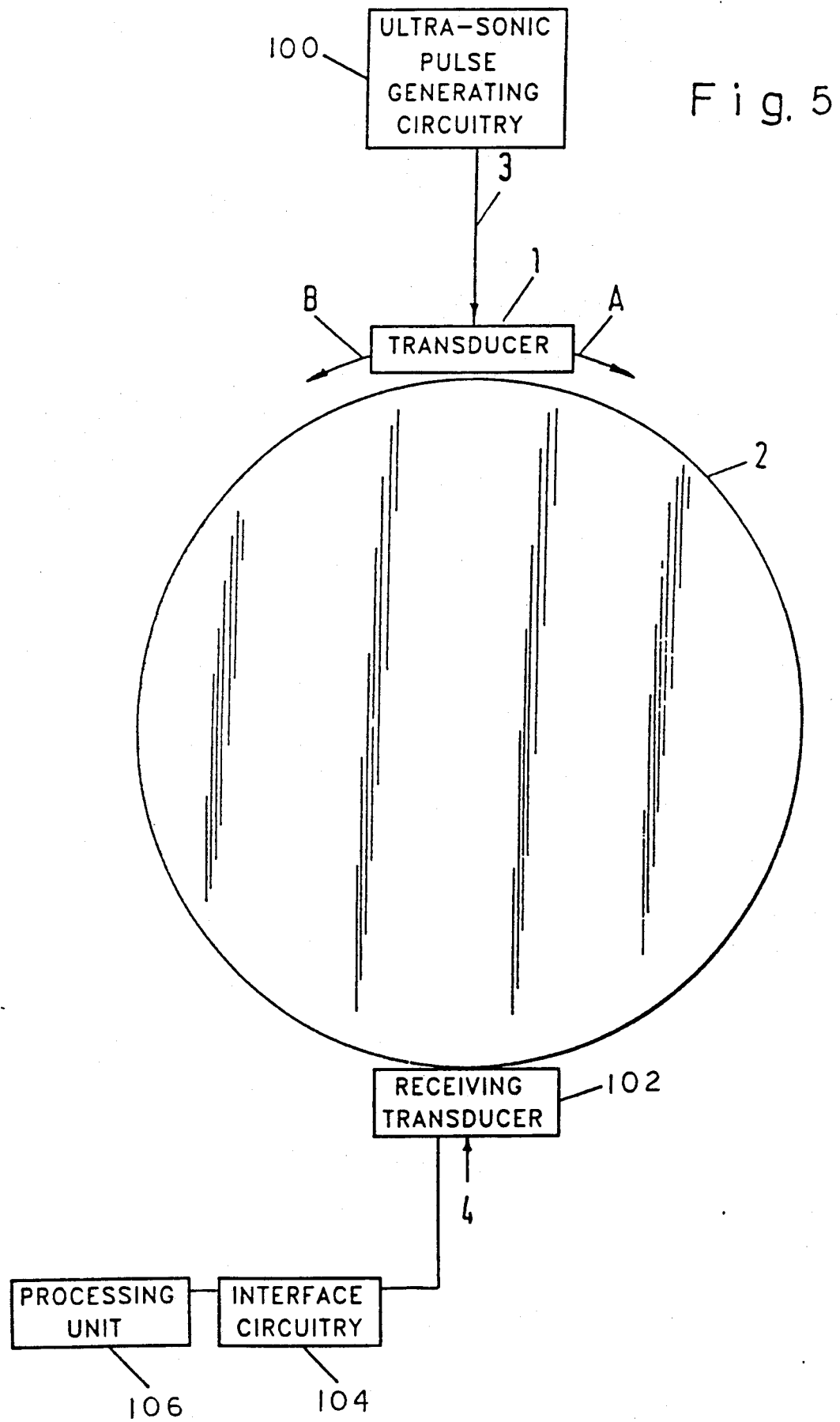
FIG. 5 shows another schematic drawing for execution of the process according to an embodiment of the invention.

FIG. 5 shows in addition to what is already shown in FIG. 1 an ultrasonic pulse generating circuitry 0100 which is connected to the transducer 1 which at least transmits the signals to be transmitted around the test piece 2. A receiving transducer assembly 102 is shown disposed at location 4 connected to this receiving transducer assembly 102. Interface circuitry 104 preferably contains a peak detector. This peak detector measures the peak signals which are received by the receiving transducer assembly 102 and tracks these peaks signals preferably up and down as the signals vary. Alternatively the peak detector could track only peak signals as opposed to up and down. Yet alternatively, the peak detector could have some sort of peak and hold circuitry which would hold a peak unit a higher peak is detected. However, there may be a reason to track the ultrasonic modulating and or the envelope of the ultrasonic signal at point 4 in order to identify the various meanings of these signals. The interface circuitry 104 also includes digitizing circuitry and output circuitry to output signals to a processing unit 106 which may be a computer.

Figure 6:
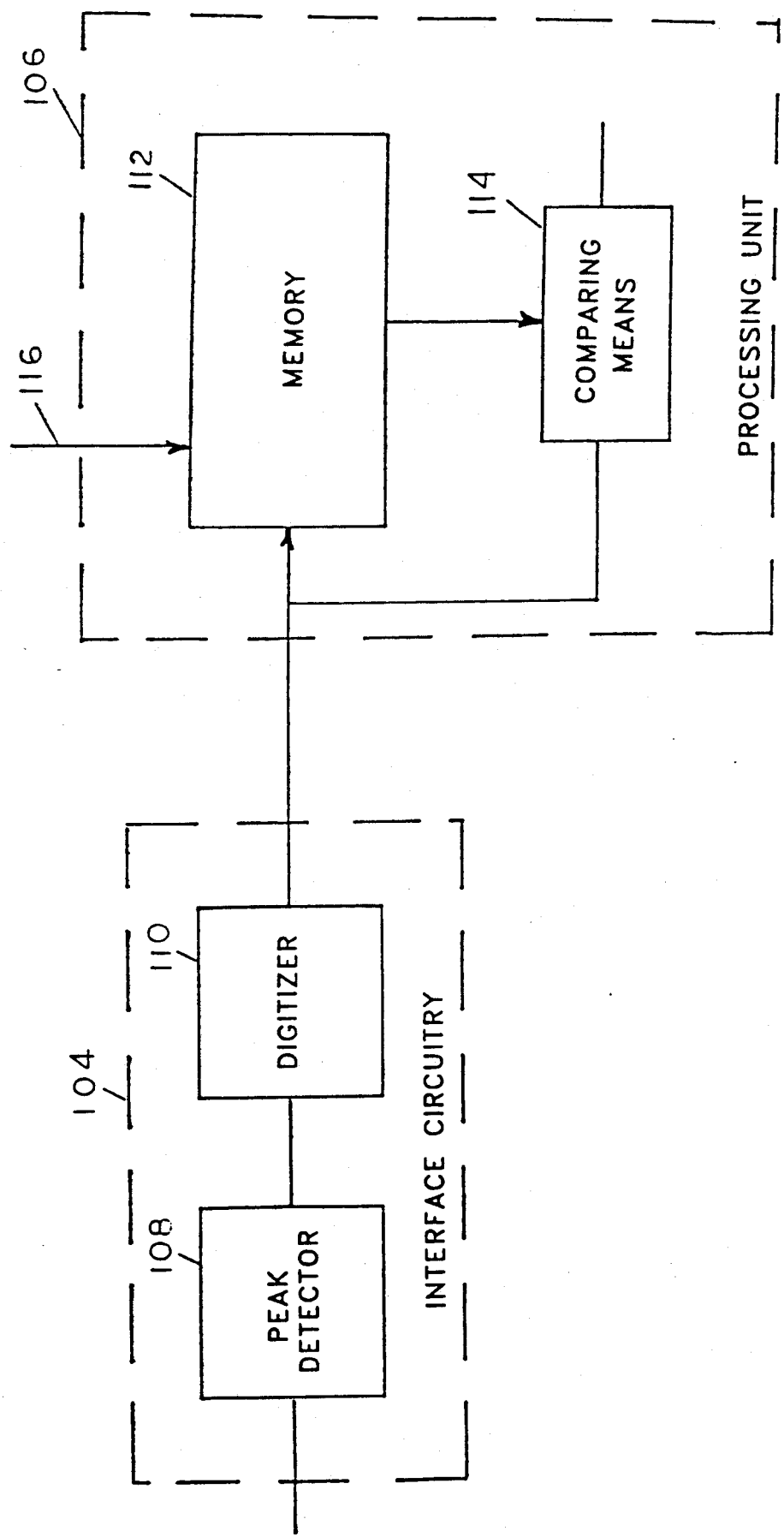
FIG. 6 is a schematic diagram of a portion of FIG 5.

Now going on to FIG. 6 the interface circuitry 104 is shown with a peak detector 108 connected to a digitizer 110. The output of the interfaced circuitry 104 is shown connected to the processing unit which preferably has a memory 112 and comparing means 114. The memory preferably contains signals which have been inputted by the transmitted signal input 116 to be stored in the memory for comparison with the digitized received signals. The signals in memory may also be prepared at an earlier time as representative signals from representative runs previously done. Also the types of discontinuities can be stored in the memory and called up at particular times when needed to compare them to the received signals. A comparison means 114 is provided which may compare the received signals which have been digitized by the digitizer 110 with the signal in memory 112.

Figure 7:
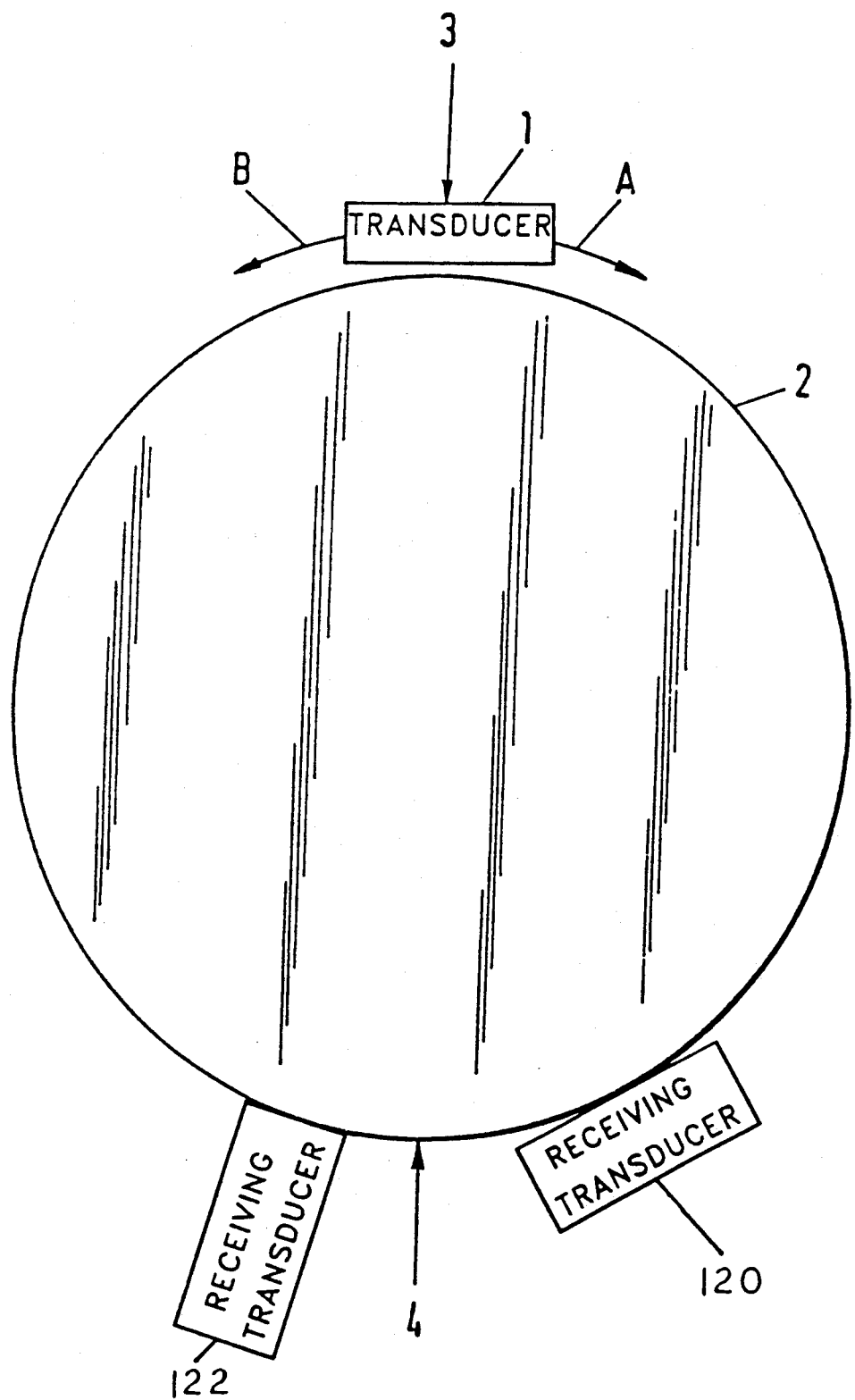
FIG. 7 shows another embodiment of the invention.

FIG. 7 shows a receiving transducers 120 and 122. One of these receiving transducers 120 and 122 is used to receive reflected pulses and the other is used to receive damped pulses or they may be adapted for receiving both damp pulses and reflected pulses with the appropriate blanking and turning on and turning off circuitry connected thereto.

There may be also a series of transmitting transducers and a series of receiving transducers for receiving the signals from each or several of the transmitting transducer. In this case, the receiving and the transmitting transducer are disposed at a plurality of locations about the test piece 2. These positions are chosen in accordance with the teachings of the present application.

An example of a bidirectional ultrasonic transmission system or method is found in U.S. Pat. No. 4,793,185 entitled "Nondestructive testing".

An example of unidirectional ultrasonic transmission system or method is found in U.S. Pat. No. 4,732,040 entitled "Electrodynamically producing ultrasonic waves".

Some examples of transducers are found in U.S. Pat. No. 4,733,207 entitled "Surface acoustic wave filters" and U.S. Pat. No. 4,333,347 entitled "Stimulating electro-acoustical transducers".

Some examples of ultrasonic testing are found in U.S. Pat. No. 4,305,297 entitled "Ultrasonic testing of wed seams of pipes for detecting transversely extending defects", U.S. Pat. No. 4,240,281 entitled "Automatic self-checking of test equipment", U.S. Pat. No. 4,238,963 entitled "Test head for ultrasonic testing of structural material" U.S. Pat. No. 4,164,150 entitled "System for inspecting tubes or pipes by means for ultrasonics", U.S. Pat. No. 4,173,897 entitled "Method of adjusting ultrasonic test systems", U.S. Pat. No. 3,861,574 entitled "Apparatus for the production and/or testing of welded helical seam pipe".

Some examples of ultrasonic testing structures are found in U.S. Pat. No. 4,162,636 entitled "Mount for ultrasonic test head".

Some examples of ultrasonic testing equipment are found in U.S. Pat. No. 4,106,326 entitled "Initialization and preparation of on -production-line ultrasonic test equipment" and U.S. Pat. No. 4,174,442 entitled "Method and apparatus for the ultrasonic detection of flaws in hot metallic objects".

In summary, one feature of the invention resides broadly in a process for the detection of discontinuities on long workpieces, in particular on tubes, rods and bars, in which the test piece is moved in the axial direction, without rotation, past at least one fixed electrodynamic transducer, and wave pulses circulating tangentially in the test piece, which spread out in both circumferential directions, are generated in pulses and received, whereby the sites of the reception and the generation of the wave pulses simultaneously travelling in both circumferential directions of the test piece are selected so that the two wave pulses travelling uninterfered produce destructive interference at the site of the receiver, characterized by the fact that for each clock pulse, the receiver signal and a burst signal having a high pulse duty factor, whose period is less than one-quarter of the revolution time of the wave pulse around the test piece, and whose length is the same as the decay time of the uninterfered wave pulse with a defect-free workpiece, are conducted to a peak detector, and the output signal of the peak detector is digitized and transferred to a computer.

Another feature of the invention resides broadly in a process characterized by the fact that alternating in the test cycle, wave pulses are generated at two separate sites and travel in both circumferential directions, and the site of the reception for the reflected pulses is different from the site of the reception for the damped pulses, and the corresponding sequences of receiver signals are evaluated separately.

Yet another feature of the invention resides broadly in an apparatus for the execution of the process with an electrodynamic transducer, having separate transmitting and receiving coils, which is connected to an evaluation unit, characterized by the fact that the apparatus has a transducer whose transmitter and receiver coils are wound on a bobbin and are offset from one another by one-quarter of the wavelength, whereby if there are several transmitter coils, all the transmitter coils are activated in the same clock pulse or cycle.

A further feature of the invention resides broadly in an apparatus characterized by the fact that in one circumferential plane, offset from one another over the circumference of test piece, there are two transducers, and the sequences of receiver signals of both transducers are conducted to an evaluation unit.

All, or substantially all, of the components and methods of the various embodiments may be used with at least one embodiment or all of the embodiments, if any, described herein.

All of the patents, patent applications, and publications recited herein, if any, are hereby incorporated by reference as if set forth in their entirety herein.

The invention as described hereinabove in the context of the preferred embodiments is not to be taken as limited to all of the provided details thereof, since modifications and variations thereof may be made without departing from the spirit and scope of the invention.

What is claimed is:

1. A process for the detection of vibrationally determinable discontinuities in elongated workpieces, said process comprising the steps of:
    positioning the workpiece in relationship to a vibrational transducer transmitting means;
    generating at least two vibrational signals with the vibrational transducer transmitting means and directing the generated vibrational signals at least around a peripheral portion of the elongated workpiece on which detection of discontinuities is being conducted;
    projecting the vibrational signals generated by the vibrational transducer means at least as two transmitted signals in substantially different directions about the workpiece;
    disposing at least one receiving transducer means at its corresponding at least one predetermined position around the workpiece;
    said at least one predetermined position being located to receive signals where at least two of the signals transmitted by said transducer means in a workpiece substantially free of any substantial discontinuities would produce at least partial destructive interference between the at least two transmitted signals;
    said transmitted signals comprising pulses;
    said transmitted signals having a cycle period of time between pulses which is substantially longer than the time corresponding to the pulse widths;
    choosing the time from the beginning of one pulse to the beginning of the next pulse of a cycle period of time of said transmitted signals as being a time less than one quarter of the time for a pulse to traverse around a peripheral portion of the elongated workpiece for a workpiece being substantially free of any substantial discontinuities;
    choosing the length of time of the pulse width of the transmitted signal to be in correspondence with the decay time of a pulse propagating in a workpiece which workpiece is substantially free of any substantial discontinuities;
    receiving said transmitted at least two generated vibrational signals at said at least one receiving transducer means which receiving transducer means is disposed at said at least one predetermined position;
    processing at least the received signals to indicate deviations from signals received from a substantially equivalent workpiece being substantially free of any substantial discontinuities in a processing unit; and
    determining at least the presence of any substantial discontinuities in the workpiece being tested in said processing unit.

2. A process for the detection of vibrationally determinable discontinuities according to claim 1 wherein said at least two transmitted signals are two signals radiating substantially in circumferentially opposite directions around the periphery of the workpiece.

3. A process for the detection of vibrationally determinable discontinuities according to claim 2 wherein said two transmitted signals are transmitted in opposite directions about the periphery of the workpiece.

4. A process for the detection of vibrationally determinable discontinuities according to claim 2 wherein the pulse width is equal to the decay time of a pulse propagating in a workpiece which workpiece is substantially free of any substantial discontinuities.

5. A process for the detection of vibrationally determinable discontinuities according to claim 1 wherein said processing processes the at least the received signals in a peak detector to generate an output signal;
    digitizing the output signal from the peak detector; and
    transferring the digitized signal to a computing means.

6. A process for the detection of vibrationally determinable discontinuities according to claim 5 includes comprising the comparing the digitized signal in the computing means to predetermined signals stored in the computing means and determining at least one of; the number, nature and condition of the discontinuities in the workpiece under test.

7. A process for the detection of vibrationally determinable discontinuities according to claim 1 including receiving different signals with different ones of said at least one receiving transducer means.

8. A process for the detection of vibrationally determinable discontinuities according to claim 1 including inputting signals corresponding to the transmitted pulses for processing in said processing unit.

9. A process for the detection of vibrationally determinable discontinuities according to claim 1 wherein said transmitted transducer means comprises two transducer transmitting mean disposed at two separate locations, the vibrational signals from each of the two transducer means generating pulses traveling in different directions and starting at the two separate locations.

10. A process for the detection of vibrationally determinable discontinuities according to claim 1 including receiving reflected pulses and receiving damped pulses.

11. A process for the detection of vibrationally determinable discontinuities according to claim 6 including receiving reflected pulses and receiving damped pulses.

12. A process for the detection of vibrationally determinable discontinuities according to claim 8 including receiving reflected pulses and receiving damped pulses.

13. A process for the detection of vibrationally determinable discontinuities according to claim 10 including receiving said reflected pulses at separate locations than said damped pulses.

14. A process for the detection of vibrationally determinable discontinuities according to claim 13 wherein said processing includes processing said reflected pulses and said damped pulses separately.

15. A process for the detection of vibrationally determinable discontinuities according to claim 9 including alternating the transmission of pulses between the two separate transducer means.

16. A process according to claim 1 including moving the workpiece and said vibrational transducer transmitting means respectively along a longitudinal axis of the workpiece.

17. Apparatus for a process for the detection of vibrationally determinable discontinuities in elongated workpiece, said apparatus comprising:

vibrational transducer transmitting means for generating at least two vibrational signals vibrational transducer transmitting means and directing the generated vibrational signals at least around a peripheral portion of the elongated workpiece on which detection of discontinuities is to be conducted;

said vibrational transducer transmitting means comprising means for projecting the vibrational signals generated by the vibrational transducer means at least as two transmitted signals in substantially different directions about the workpiece;

at least one receiving transducer means at its corresponding at least one predetermined position around the workpiece;

said vibrational transducer transmitting means for being located at at least one predetermined position for receiving signals; said vibrational transducer transmitting means for being located where at least two of the signals transmitted by said transducer means in a workpiece substantially free of any substantial discontinuities would produce at least partial destructive interference between the at least two transmitted signals;

said vibrational transducer transmitting means comprising means for generating said transmitted signals as pulses;

said transmitted signals for having a cycle period of time between pulses which is substantially longer than the time corresponding to the pulse widths;

said vibrational transducer transmitting means having means for setting the time from the beginning of one pulse to the beginning of the next pulse of a cycle period of time of said transmitted signals for being a time less than one quarter of the time for a pulse to traverse around a peripheral portion of the elongated workpiece for a workpiece being substantially free of any substantial discontinuities;

said vibrational transducer transmitting means having means for setting the length of time of the pulse width of the transmitted signal to be in correspondence with the decay time of a pulse propagating in a workpiece which workpiece is substantially free of any substantial discontinuities;

said at least one receiving transducer means for receiving said transmitted at least two generated vibrational signals at said at least one receiving transducer means which at least one receiving transducer means is for being disposed at said at least one predetermined position; and a processing unit for processing at least the received signals and for indicating deviations from signals received from a substantially equivalent workpiece being substantially free of any substantial discontinuities;

said processing unit comprising means for determining at least the presence of any substantial discontinuities in the workpiece being tested in said processing unit.

18. Apparatus for a process for the detection of vibrationally determinable discontinuities according to claim 17 wherein said processing unit comprising a peak detector, a digitizer connected to said peak detector to generate digitizing signals and comparison means for comparing the digitized signals to predetermined representation of signals.

19. Apparatus for a process for the detection of vibrationally determinable discontinuities according to claim 18 including means for respectively moving the workpiece and said vibrational transducer transmitting means along a longitudinal axis of the workpiece.

* * * * *